(12) United States Patent
Harburn et al.

(10) Patent No.: US 7,189,198 B2
(45) Date of Patent: Mar. 13, 2007

(54) MAGNETICALLY GUIDABLE CARRIERS AND METHODS FOR THE TARGETED MAGNETIC DELIVERY OF SUBSTANCES IN THE BODY

(75) Inventors: Jonathan Harburn, St. Louis, MO (US); Rogers C. Ritter, Charlottesville, VA (US)

(73) Assignee: Stereotaxis, Inc., St. Louis, MO (US)

( * ) Notice: Subject to any disclaimer, the term of this patent is extended or adjusted under 35 U.S.C. 154(b) by 719 days.

(21) Appl. No.: 10/613,921

(22) Filed: Jul. 3, 2003

(65) Prior Publication Data

US 2004/0096511 A1    May 20, 2004

Related U.S. Application Data

(60) Provisional application No. 60/393,681, filed on Jul. 3, 2002.

(51) Int. Cl.
*A61N 2/00* (2006.01)
(52) U.S. Cl. .......................................................... 600/9
(58) Field of Classification Search ............... 600/9–15; 128/897–899
See application file for complete search history.

(56) References Cited

U.S. PATENT DOCUMENTS

| | | | |
|---|---|---|---|
| 4,758,275 A * | 7/1988 | Yubakami et al. | 106/31.32 |
| 5,921,244 A * | 7/1999 | Chen et al. | 128/897 |
| 6,231,496 B1 * | 5/2001 | Wilk et al. | 600/9 |
| 6,296,604 B1 | 10/2001 | Garibaldi et al. | |
| 6,315,709 B1 | 11/2001 | Garibaldi et al. | |
| 6,364,823 B1 | 4/2002 | Garibaldi et al. | |
| 6,375,606 B1 | 4/2002 | Garibaldi et al. | |
| 6,961,620 B2 * | 11/2005 | Rioux et al. | 607/99 |

* cited by examiner

*Primary Examiner*—John P. Lacyk
(74) *Attorney, Agent, or Firm*—Harness, Dickey & Pierce, P.L.C.

(57) ABSTRACT

A method of delivering a substance to targeted tissue comprising the steps of: delivering a plurality of magnetically responsive particles which are carrying the substance and have a hydrophobic coating into the patient's vasculature upstream of the targeted tissue; and applying a magnetic gradient in the vicinity of the targeted tissue to draw the magnetically responsive particles against the wall of the patient's vasculature in the vicinity of the targeted tissue, to allow the substance on the magnetic particles to migrate through the wall of the patent's vasculature to targeted tissue.

24 Claims, 1 Drawing Sheet

MAGNETICALLY GUIDABLE CARRIERS AND METHODS FOR THE TARGETED MAGNETIC DELIVERY OF SUBSTANCES IN THE BODY

CROSS-REFERENCE TO RELATED APPLICATION

This Application claims priority of U.S. Provisional Patent Application Ser. No. 60/393,681, filed Jul. 3, 2002, incorporated herein by reference

FIELD OF THE INVENTION

This invention relates to the targeted delivery of substances with the body through the use of magnetically guidable carriers.

BACKGROUND OF THE INVENTION

It has long been proposed to target the delivery of a substance within the body by associating the substance with magnetically responsive carriers (for example magnetite particles) and using magnetic fields and/or gradients to control the carriers, and thus the delivery of the substance. For example, it has been proposed to deliver an antitumor medication to a tumor by coating magnetite particles with the substance, introducing the particles into the patient's blood stream, and guiding the coated magnetite particles to the tumor site with a magnet.

However this method of delivery has been difficult to achieve in practice with very small particles. This is possibly due to the fact that the fluid forces on small particles are much higher than the magnetic forces that can be practically applied to such particles. According to Stokes law the fluid forces on a particle re give by $$F_R = 6\pi v \eta r$$

where: $\eta$=viscosity
v=velocity
r=radius

The magnetic forces are:

$$F_M = m\, dB/dz = MV dB/dZ = M(4/3)\pi r^3 dB/dZ$$

where m is the particle magnetic moment, M its magnetization, V its volume, and dB/dZ is the applied magnetic gradient.

Setting the fluid forces equal to the magnetic forces:

$$F_R = F_M$$

$$6\pi v \eta r = M 4/3 \pi r^3 dB/dZ$$

$$dB/dZ = 9/2\ v\eta/Mr^2$$

This gives the gradient needed to control a single particle of radius r, magnetization M, in a stream of velocity v, with viscosity $\eta$. If $\eta$=0.04 poise (for blood), and stream velocity is 100 cm/sec, M=450 emu/cm$^3$, and r=2×10$^{-4}$ cm, a gradient of 4×10$^6$ oersted/cm or 400 T/m is needed to hold the particle in the stream. This magnetization is for pure magnetite. Typical particles might be 10 percent magnetite by volume, so another factor of 10 would be needed for the gradient.

Thus, the magnetic control of small magnetic carrier particles in the bloodstream is difficult, requiring impracticably large gradients.

SUMMARY OF THE INVENTION

The present invention relates to a method of delivering a substance to targeted tissues in the body. Generally, the method comprises delivering the substance on magnetically responsive carrier particles that have a hydrophobic outer layer. This outer layer is immiscible with the hydrophilic character of the blood, and it is believed that together with entanglement among the layers of the individual particles these act a shield preventing their separation.

The particles are preferably delivered to the patient's vasculature upstream of the target site. A magnetic gradient is applied in the vicinity of the targeted tissue to draw the flexibly conjoined magnetic carrier particles against the wall of the patient's vasculature in the vicinity of the targeted tissue, to allow the substance on the magnetic particles to migrate through the wall of the patent's vasculature to targeted tissue.

In one preferred embodiment, the hydrophobic coating is removable, i.e. is connected to the particles with scissile bonds. Thus, once in the vicinity of the target tissue, the hydrophobic layers can be cut, to expose a less hydrophobic surface, and preferably a hydrophyllic surface. This less hydrophobic surface facilitates the release of the substance being carried, and possibly its delivery through the vasculature to the targeted tissue.

An aspect of this invention is the hydrophobic containment of the particles in the bloodstream provides a coherent force on a group of particles so that smaller, reasonably obtainable magnetic gradients are able to control the particles as a group. Another aspect of this invention is conversion of the particles to a less hydrophobic nature to facilitate the release and/or uptake of the substance.

DETAILED DESCRIPTION OF THE PREFERRED EMBODIMENT

Figure 1:
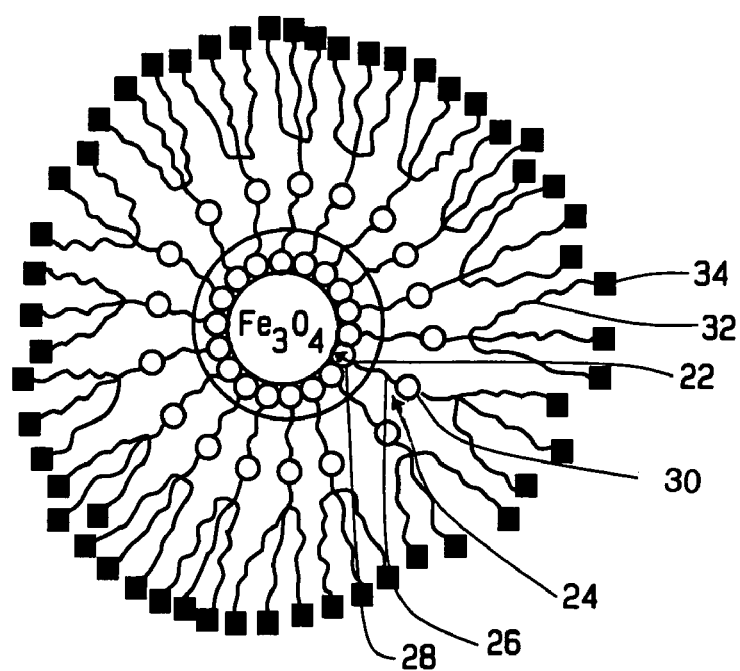
FIG. 1 is a schematic view of a coated particle in accordance with the principles of the present invention.

In a first aspect, this invention relates to a method of delivering a substance to targeted tissues in a patient's body. This substance may be a therapeutic or diagnostic material. According to the method of the present invention, a plurality of magnetically responsive carrier particles having hydrophobic coating or layer are used. The substance is carried on the particles, for example on the molecules that form the coating. The coating is believed important in two respects, it preserves an desired intraparticle distance to prevent undesirable agglomeration of the particles in when a magnetic field or gradient is applied. The coating is also important to loosely agglomerating the particles into a controllable mass through interactions between the coatings of adjacent particles, and through action in the generally hydrophilic blood.

In the preferred embodiment, the coated particles carrying the substance to be delivered to the targeted tissue is delivered to the patient's vasculature upstream of the targeted tissues. A magnetic gradient is applied in the vicinity of the targeted tissue to draw the magnetic carrier particles against the wall of the patient's vasculature in the vicinity of the targeted tissue, to allow the substance on the magnetic particles to migrate through the wall of the patent's vasculature to targeted tissue.

The magnetic carrier particles are preferably magnetite ($Fe_3O_4$) particles but could also be hematite ($Fe_2O_3$), cobalt, iron, mixtures or alloys thereof, or other magnetic particles which could be made biologically compatible with coatings. It would be desirable if the particles were radiopaque, so that the delivery of the particles could be monitored by x-ray or fluoroscope. Thus the particles could include, for example, barium in the form of a barium iron oxide.

The magnetically responsive carrier particles are preferably generally spherical, but could be some other shape (e.g. oblong or needlelike). The maximum diameter (or dimension in the case of non-spherical particles) is preferably less than about 70 nm, and more preferably less than about 30 nanometers. The hydrophobic coating can be implemented by attaching molecules with hydrophobic ends to the participles, and preferably molecules comprising a hydrophobic group joined with a less hydrophobic group (or even a hydrophilic group) with a scissile bond. Thus as shown schematically in FIG. 1, a core 22 of magnetite (or other suitable magnetically responsive material) is surrounded by a plurality of molecules 24 comprising a hydrophyllic group 26 having has a polar head 28. The polar head 28 might be, for example, a carboxylate sulfonate, phosphonic acid, phosphonate, or other negative counterion. The hydrophilic portion might be a polyacid, such as polyacrylic acid, polymethlyacrylic acid, polylactic acid, polyphonate, polyphosphinic acid, polyphosphonate. The hydrohilic group may be biodegradable, for example polylachiacid-glycolic acid copolymer or polyanhydrides.

A scissile bond 30 joins a bridging group 32, such as a trihydroxymethylamime, or triamine methano, glyceride to the hydrohyllic (or less hydrophobic) groups 26. The scissile bond may be an amide or ester bond, or any anhydride coupling, or any bond that can be cleaved or allowed to cleave. For example, the scissile bond may be cleaved by the action of naturally occurring proteases in the body, or by the action of chemicals, thermal energy, electromagnetic radiation, or sonic (e.g. ultrasound). Preferably, a plurality of hydrophobic groups 34 attach to the bridging group 32. These hydrophobic groups may be, for example polypropylene oxide or some other material that is immiscible in blood but which is biocompatible.

A wide variety of diagnostic and therapeutic substances can be associated with the carrier particles, including anti-cancer agents such as Adriamycin, BiCNU, Carboplatinum, Daunorubicin, DTIC, Fludarabine, Gemcitabine, Idarubicin, Irinotecan, Mithramycin, Mitomycin, Mitoxantrone, Navelbine, Nitrogen Mustard, Taxol, Taxotere, Topotecan, Velban, Vincristine, VP-16; or radionuclides with a covalently bound chelator e.g. DPTA or DOTA; photodynamic therapy drugs e.g. Phthalocyanines; Gene Vectors which may be bound to a covalently bound chelator (e.g. Streptavadin): Tumor Necrosis Factors; Clot busting drugs: Alteplase or TPA (brand name: Activase), Streptokinase (Streptase or Kabikinase), Urokinase (Abbokinase), Anistreplase (Eminase), Reteplase (Retavase); Steroids; and Antibiotics; Tumor necrosis and antiangiogenesis agents.

The substance can be bonded to branches on the hydrophilic layer, or can simply be physically associated in the midst of the hydrophilic layer, trapped by the surrounding hydrophobic layer.

Figure 2:
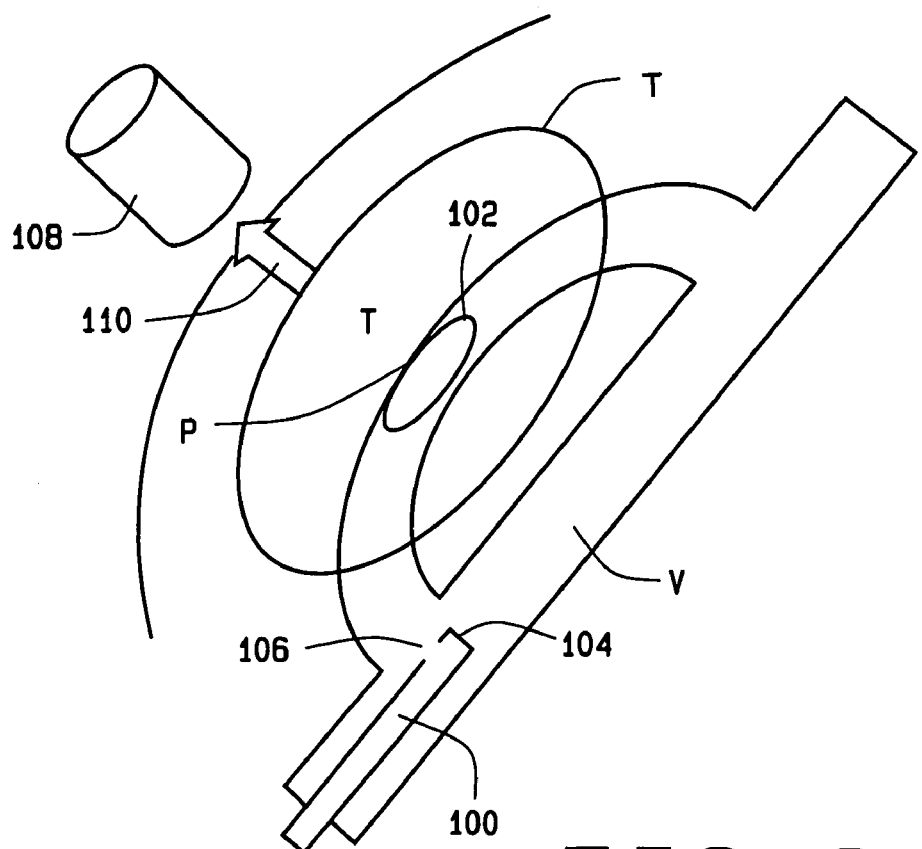
FIG. 2 is diagram illustrating the method of the present invention

One example of a specific procedure is the delivery of one of an antitumor medcation to a tumor in a patient, is illustrated schematically in FIG. 2. A catheter 100 is navigated through the subject's vasculature V to a location upstream of the subject's tumor T. The catheter 100 can be navigated directly (it may be mechanically navigated, or it may alternatively be magnetically navigated by providing a magnet on the distal end of the catheter, by using the bulk magnetism of the carrier particles in the distal end of the lumen or by providing a magnet on a stylette or tether in the distal end of the lumen. Alternatively, a guide wire can be navigated through the subject's vasculature (either mechanically or magnetically, as described above), to a location upstream of the blood stream to the tumor. A catheter can then be advanced over the guidewire to the site.

In a preferred embodiment of the procedure, the catheter 100 is advanced through the subject's vasculature as close as possible to the tumor T. Once at the appropriate site, or at each appropriate site, a mass 102 of magnetically responsive particles with a hydrophobic coating carrying the antitumor substance are released into the blood stream. Preferably the distal tip 104 of the catheter 100 will be closed, and a side hole 106 on the tissue side used to deliver the fluid the smallest possible distance to the vessel wall, to minimize downstream migration. An externally applied magnetic field can be applied with an external magnet 108 to properly orient the catheter for optimum delivery. (A heavy metal stripe at the catheter tip might be necessary to enable the physician to orient this hole to the side of the tissue.) A magnetic gradient is applied at a point P adjacent the targeted tissue T in a direction transverse to the flow direction through the blood vessel to draw the ejected mass of material against the vessel wall toward the target tissue T. This allows the substance to migrate from the particles. Alternatively, the hydrophobic coating could be formed of hydrophobic groups joined to the particles with scissile bond. These bonds can be cleaved to remove the hydrophobic layer and expose a less hydrophobic/more hydrophilic layer. The magnetic gradient indicated as arrow 110 can be applied with a permanent magnet, an electromagnet, or even a superconducting electromagnet, indicated as 108. The gradient is preferably no more than about 10 T/m, and more preferably no more than about 5 T/m and most preferably no more than about 1 T/m, and preferably the particles can be held with a gradient as low as 0.5 T/m. The gradient is applied at least until a sufficient fraction of the injected particles have traveled to the delivery site.

One example of formation of an outer hydrophobic layer is illustrated in FIG. 1. As shown in FIG. 1, magnetite particles with a coating having a generally hydrophilic inner portion and a generally hydrophobic outer portion. The hydophilic inner portion is preferably separable from the hydrophobic outer portion. The coating may be formed by a plurality of branched molecules, comprising a plurality of hydrophilic molecules with polar heads which bond to the magnetite particles. In the preferred embodiment the magnetite core might have a diameter of about 0 nm, a hydrophyllic layer of about 3 mm, and a hydrophobic layer of about 5 to about 7 nm.

The scissile bond may be an amide or ester corresponding to the covalent boding of any amino acid, including peptides, proteins, DNA, antibodies, and genes. Water soluble substances can be loaded into and carried by the hydrophilic portion of the coated particles.

The scissile bond may be thermo-responsive, and may be cleaved using AC magnetic field, increasing the temperature by 10° in thirty seconds. The scissile bonds may also be cleaved by electromagnetic radiation, directly or indirectly. Directly, for example by ultraviolet light or other radiation cleavage by fiberoptic. Indirectly, for example by IR transdermally to activation of PDT drugs to release singlet oxygen or radiation cleavage at certain wavelengths. The scissile bond may also be cleavable by other external input, such as ultrasound. There may be multiple scissile bonds. Several chains of drugs, amino acids, proteins, genes, enzymes, etc. may be coupled together in order to give multiple therapies.

If the particles are designed with a specific pore size on the outer hydrophobic layer, the particles may degrade on the inside to release drugs through the pores while maintaining structural integrity and still directable using the magnetic core.

While the above description reference the targeted delivery of substances to a tumor, the invention is not so limited, and can used to deliver any substance to any location or tissue in the body where a magnetic gradient can be applied.

What is claimed is:

1. A method of delivering a substance to targeted tissue comprising the steps of:
   delivering a plurality of magnetically responsive particles which are carrying the substance and have a hydrophobic coating into the patient's vasculature upstream of the targeted tissue, wherein the particles include a less hydrophobic layer under the hydrophobic layer, wherein the hydrophobic layer is at least partially removable; and further comprising the step of at least partially removing the hydrophobic layer after the particles are at the delivery site to facilitate the release of the substance; and
   applying a magnetic gradient in the vicinity of the targeted tissue to draw the magnetically responsive particles against the wall of the patient's vasculature in the vicinity of the targeted tissue, to allow the substance on the magnetic particles to migrate through the wall of the patent's vasculature to targeted tissue.

2. The method according to claim 1 wherein the step of delivering the particles into the patient's vasculature comprises navigating the distal end of a catheter to a point in the patient's vasculature that is upstream of the targeted tissue, and ejecting the particles from the catheter.

3. The method according to claim 1 wherein the step of delivering the particles into the patient's vasculature comprises navigating the distal end of a guidewire to a point in the patient's vasculature that is upstream of the targeted tissue, advancing the distal end of the catheter over the guidewire, and ejecting the particles from the catheter.

4. The method according to claim 1 wherein the magnetically responsive particles are less than about 20 nm in diameter.

5. The method according to claim 1 wherein the magnetically responsive particles are less than about 10 nm in diameter.

6. The method according to claim 1 wherein the magnetically responsive particles have an average diameter less than about 20 nm in diameter.

7. The method according to claim 1 wherein the magnetically responsive particles are less than 10 nm in diameter.

8. The method according to claim 1 wherein the magnetic particles have an average largest dimension of less than 40 nanometers.

9. The method according to claim 1 wherein the magnetic particles have an average largest dimension of less than 25 nanometers.

10. The method according to claim 1 wherein the magnetic particles comprise magnetite.

11. The method according to claim 1 wherein the magnetic particles comprise a barium iron oxide.

12. The method according to claim 1 wherein the magnetic particles comprise a radiopaque material.

13. The method according to claim 1 wherein the hydrophobic layer is about 10 nanometers thick.

14. The method according to claim 1 wherein the hydrophobic layer is about 5 nanometers thick.

15. A method of delivering a substance to a targeted tissue comprising the steps of:
    delivering a plurality of magnetically responsive particles which are carrying the substance and having a hydropgobic coating into the patient's vasculature upstream of the targeted tissue, wherein particles include a hydrophilic layer under the hydrophobic layer, wherein the hydrophobic layer is at least partially removable; and further comprising the step of at least partially removing the hydrophobic layer after the particles are at the delivery site to facilitate the release of the substance; and
    applying a magnetic gradient in the vicinity of the targeted tissue to draw the magnetically responsive particles against the wall of the patient's vasculature in the vicinity of the targeted tissue, to allow the substance on the magnetic particles to migrate through the wall of the patent's vasculature to targeted tissue.

16. The method according to claim 15 wherein the step of at least partially removing the hydrophobic layer includes allowing naturally occurring proteases to sever the hydrophobic layer from the hydrophilic layer.

17. The method according to claim 15 wherein the step of at least partially removing the hydrophobic layer includes breaking scissile bonds between the hydrophobic and hydrophilic layers by applying at least one of a chemical agent, thermal energy, electromagnetic radiation, or sonic energy.

18. A magnetically guided carrier composition for carrying a substance, the composition comprising a plurality of particles, each comprising a magnetically responsive core, surrounded by a outer hydrophobic layer that is at least partially removable, and an inner hydrophilic layer.

19. The magnetically guided carrier composition according to claim 18 wherein the hydrophilic layer and the hydrophobic layer are formed by a hydrophilic group and a hydrophobic group joined by a scissible bond.

20. The magnetically guided carrier composition of claim 18 wherein the scissible bond is cleavable upon an increase of temperature.

21. The magnetically guided carrier composition of claim 18 wherein the scissible bond is cleavable upon application of uv light.

22. The magnetically guided carrier composition of claim 18 wherein the hydrophilic group consists of a polyacid.

23. The magnetically guided carrier composition of claim 18 wherein the hydrophopic group consists of a biocompatible hydrophobic polymer.

24. The magnetically guided carrier composition of claim 19, wherein the hydrophobic layer comprises a hydrophobic group having bonds that are cleavable to yield a hydrophilic-layered particle capable of being removed through renal excretion.

* * * * *